United States Patent [19]
Elsberry et al.

[11] Patent Number: 6,042,579
[45] Date of Patent: *Mar. 28, 2000

[54] TECHNIQUES FOR TREATING NEURODEGENERATIVE DISORDERS BY INFUSION OF NERVE GROWTH FACTORS INTO THE BRAIN

[75] Inventors: Dennis D. Elsberry, Plymouth; Mark T. Rise, Monticello, both of Minn.

[73] Assignee: Medtronic, Inc., Minneapolis, Minn.

[ * ] Notice: This patent is subject to a terminal disclaimer.

[21] Appl. No.: 08/846,810

[22] Filed: Apr. 30, 1997

[51] Int. Cl.⁷ .............................. A61M 11/00; A61M 9/22
[52] U.S. Cl. .......................... 604/891.1; 604/503; 604/93
[58] Field of Search .............................. 604/890.1, 891.1, 604/65–67, 49–51, 502, 503, 522, 93; 128/898; 600/544, 378, 411

[56] References Cited

U.S. PATENT DOCUMENTS

| | | | |
|---|---|---|---|
| 4,003,379 | 1/1977 | Ellinwood, Jr. | 128/260 |
| 4,146,029 | 3/1979 | Ellinwood, Jr. | |
| 4,692,147 | 9/1987 | Duggan | |
| 5,011,472 | 4/1991 | Aebischer et al. | |
| 5,025,807 | 6/1991 | Zabara | |
| 5,106,627 | 4/1992 | Aebischer et al. | |
| 5,293,879 | 3/1994 | Vonk et al. | |
| 5,462,525 | 10/1995 | Srisathapat et al. | |
| 5,474,547 | 12/1995 | Aebischer et al. | |
| 5,558,640 | 9/1996 | Pfeiler et al. | 604/67 |
| 5,639,275 | 6/1997 | Baetge et al. | 604/891.1 |
| 5,643,207 | 7/1997 | Rise | |
| 5,711,316 | 1/1998 | Elsberry et al. | 128/898 |
| 5,735,814 | 4/1998 | Elsberry et al. | 604/43 |
| 5,792,110 | 8/1998 | Cunningham | 604/158 |

FOREIGN PATENT DOCUMENTS

| | | |
|---|---|---|
| 0450386A2 | 9/1991 | European Pat. Off. |
| WO9007341 | 7/1990 | WIPO |
| WO9306116 | 4/1993 | WIPO |
| WO9308828 | 5/1993 | WIPO |
| WO9401166 | 1/1994 | WIPO |

OTHER PUBLICATIONS

Alexander et al., "Basal ganglia thalamocortical circuits: Parallel substrates for motor, oculomotor, 'prefrontal' and 'limbic' functions," Progress in Brain Research, vol. 85, pp. 119–146 (1990).

Appel, "Exitotixic Neuronal Cell Death in Amyotrophic Lateral Sclerosis", TINS, vol. 16, No. 1 (1993).

Appel, "A Unifying Hypothesis for the Cause of Amyotrophic Lateral Sclerosis, Parkinsonism, and Alzheimer Disease", Annals of Neurology, ovl. 10: No. 6: 449–505 (Dec. 1981).

Couratier et al., "Cell Culture Evidence for Neuronal Degeration in Amyotrophic Lateral Sclerosis Being Linked to Glutamate AMPA/Kainate Receptors", The Lancet, 341, pp. 265–268 (1993).

Graham, et al., Injection of Excitatory Amino Acid Antagonists Into the Medial Pallidal Segment of a 1–Methyl–4–Phenyl–1,2,3,6–tetrahydropyridine (MPTP) Treated Primate Reverses Motor Symptoms of Parkinsonism, Life Sciences, vol. 47, pp. PL–91–PL–97 (1990).

Kroll, et al., "Increasing Volume of Distribution to the Brain with Interstitial Infusion: Dose, Rather Than Convection, Might Be the Important Factor", Neurosurgery, vol. 38, No. 4, pp. 746–754 (1996).

Osorio et al., "A Method for Accurate Automated Real–Time Seizure Detection," Epilepsia, vol. 36, Supplement 4 (1995).

(List continued on next page.)

Primary Examiner—Corrine McDermott
Assistant Examiner—Michael J. Hayes
Attorney, Agent, or Firm—Banner & Witcoff, Ltd.

[57] ABSTRACT

Techniques for infusing nerve growth factors into the brain to treat neurodegenerative disorders by means of an implantable pump and catheter. A sensor is used to detect an attribute of the nervous system which reflects the degeneration of the nerve cells. A microprocessor algorithm analyzes the output from the sensor in order to regulate the amount of growth factor delivered to the brain.

23 Claims, 3 Drawing Sheets

OTHER PUBLICATIONS

Rothman et al., "Excitotoxicity and the NMDA receptor" *Trends Neuroscience* 10, pp. 229–302 (1990).

Schiff et al., "Controlling chaos in the brain," *Nature* vol. 370, pp. 615–620 (1994).

van Horne et al., "Multichannel semiconductor–based electrodes for in vivo electrochemical and electrophysiological studies in rat CNS", *Neuroscience Letters* 120, pp. 249–252 (1990).

Friedman, W.J. et al., Differential actions of neurotrophins in the locus coeruleus and basal forebrain, *Experimental Neurology* 119, pp. 72–78 (1993).

Hagg, T. and S. Varon, Ciliary neurotrophic factor prevents deneration of adult rat substantia nigra dopaminergic neurons in vivo, Proceedings National Academy of Science, USA 90 pp. 6315–6319 (1993).

Henderson, C.E., et al., Neurotrophins promote motor neuron servival and are present in embryonic limb bud, *Nature* 363 pp. 266–270 (1993).

Knusel, B., et al., Brain–derived neurotrophic factor administration protects basal forebrain cholinergic but not nigral dopaminergic neurons from degenerative changes after axotomy in the adult rat brain, *Journal of Neuroscience* 12(11) pp. 4391–4402 (1992).

Koliatsos, V.E. et al., Highly selective effects of nerve growth factor, brain–derived neurotrophic factor, and neurotrophin–3 on intact and injured basal forebrain magnoclular neurons, *Journal of Comparative Neurology* 343 pp. 247–262 (1994).

Lapchak, P. A., Nerve growth factor pharmacology: Application to the treatment of cholinergic neurodeneration in Alzheimer's disease, *Experimental Neurology* 124 pp. 16–20 (1993).

Lapchak, P.A., et al., Biology of glial cell line–derived neurotrophic factor (GDNF): Implications for the use of GDNF to treat Parkinson's disease, *Neurodegeneration* 5 pp. 197–205 (1996).

Olson, L. et al., Intraputaminal infusion of nerve growth factor to support adrenal medullary autografts in Parkinson's disease, *Archives of Neurology* 48 pp. 373–381 (1991).

Pelleymounter, M. A. and Cullen M. J., The effects of intraseptal brain–derived neurotrophic factor on cognition in rats with MS/DB lesions, *Annals New York Academy of Sciences* 679 pp. 299–305 (1993).

Seiger, et al., Intracranial infusion of purified nerve growth factor to an Alzheimer patient: The first attempt of a possible future treatment strategy, *Behavioral Brain Research* 57 (2) pp. 255–261 (1993).

Sendtner, M. et al., Actions of CNTF and neurotrophins on degenerating motoneurons: preclinical studies and clinical implications, *Journal of Neurological Sciences* 124 (Supp) pp. 77–83 (1994).

Tomac, A., et al., Protection and repair of the nigrostriatal dopaminergic system by DGNF in vivio, *Nature* 373 pp. 335–346 (1995).

Widmer, H. R. et al., BDNF protection of basal forebrain cholinergic neurons after axotomy: complete protection of p75NGFR–positive cells, *Neuroreport* 4 pp. 363–366 (1993).

Zhang, Y., et al., Basic FGF, NGF, and IGFs protect hippocampal and cortical neurons agains iron–induced deneration, *Journal of Cerebral Blood Flow and Metabolism* 13 pp. 378–388 (1993).

Stewart, S. S., et al., Trophic factors in neurologic disease, *Annual in Medicine* 39 pp. 193–201 (1988).

TECHNIQUES FOR TREATING NEURODEGENERATIVE DISORDERS BY INFUSION OF NERVE GROWTH FACTORS INTO THE BRAIN

BACKGROUND OF THE INVENTION

1. Field of the Invention

This invention relates to brain infusion techniques, and more particularly relates to such techniques for treating neurodegenerative disorders.

2. Description of Related Art

PCT Publication Number WO 93/06116, filed Sep. 17, 1992 (the "'116 Publication"), suggests the use of GDNF for preventing and treating nerve damage and nerve related diseases, such as Parkinson's disease, by implanting into the brains of patients cells that secrete GDNF. Certain membrane devices are described for such implantation.

PCT Publication Number WO 93/08828, filed Nov. 6, 1992 (the "'828 Publication"), suggests the intravenous application of certain nerve growth factors for the treatment of neuronal damage associated with ischemia, hypoxia or neurodegeneration, and teaches that intracerebroventricular administration is to be avoided because it is "difficult to implement and is associated with [a] relatively high degree of risk compared to intravenous administration." (P. 5, lines 15–17.)

PCT Publication Number WO 90/07341, filed Jan. 5, 1990 (the "'341 Publication"), states that nerve growth factor (NGF) has been demonstrated to be a neurotropic factor for the forebrain cholinergic nerve cells that die during Alzheimer's disease and with increasing age. The '341 Publication also states that experiments in animals demonstrate that NGF prevents the death of forebrain cholinergic nerve cells after traumatic injury and that NGF can reverse cognitive losses that occur with aging.

European Patent Application EP 0450386 A2, filed Mar. 18, 1991 (the "386 A2 Publication"), suggests the use of Brain Derived neurotrophic Factor (BDNF) from recombinantly derived biologically active forms for treatment of Alzheimer's disease. BDNF promotes the survival of motor neurons in several species (Henderson, C. E., et al., 1993, *Nature* 363, 277), and also promotes the survival of cholinergic neurons of the basal forebrain following frimbrial transections (Knusel, B., et al., 1992, *J. Neuroscience* 12, 4391–4402).

None of the foregoing PCT Publications teaches an adequate delivery system for the administration of any nerve growth factor, or prescribes brain sites for effective administration of nerve growth factors. In addition, they do not suggest how the dosage of nerve growth factor can be effectively regulated during infusion. The present invention is directed to these difficulties which the prior art fails to address.

SUMMARY OF THE INVENTION

A preferred form of the invention can treat a neurodegenerative disorder, such as Parkinson's disease, Alzheimer's disease or Amyotrophic Lateral Sclerosis (ALS), by means of an implantable pump and a catheter having a proximal end coupled to the pump and having a discharge portion for infusing into the brain therapeutic dosages of the one or more nerve growth factors. The catheter is implanted in the brain so that the discharge portion lies adjacent to a predetermined infusion site of the brain, such as the neuropil, the intraventricular space or the subarachnoidal space. The pump is operated to discharge a predetermined dosage of the one or more nerve growth factors through the discharge portion of the catheter into the infusion site. By using the foregoing method, the neurodegeneration that occurs in diseases, such as Parkinson's disease, Alzheimer's disease and Amyotrophic Lateral Sclerosis, can be alleviated or prevented.

Another form of the invention uses a sensor in combination with the implantable pump and catheter to administer one or more nerve growth factors in order to treat or prevent a neurodegenerative disorder. In this form of the invention, the sensor generates a signal relating to an attribute of the nervous system which indicates the degeneration of the degenerating neurons or the degeneration of neurons related to the degenerating neurons. Control means responsive to the sensor signal regulate the therapeutic dosage. For example, the dosage can be increased in response to an increase in the hyperexcitation of the neurons and can be decreased in response to a decrease in the hyperexcitation of the neurons.

By using the foregoing techniques, neurodegeneration can be controlled to a degree unattainable by prior art methods or apparatus.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
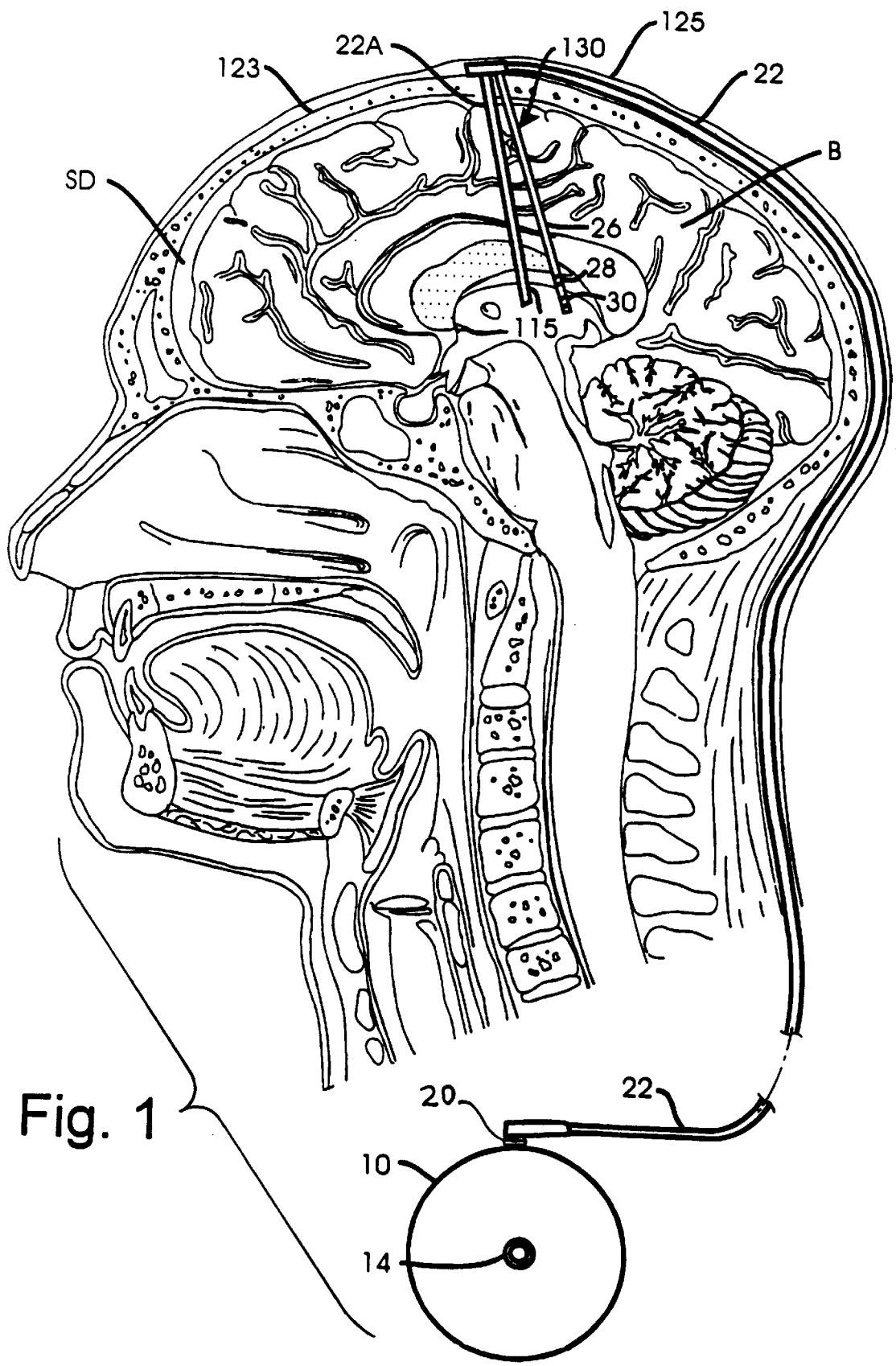
FIG. 1 is a diagrammatic illustration of a portion of the nervous system of the human body in which a preferred form of hyperexcitation sensor, pump and catheter have been implanted.

Referring to FIG. 1, a system or device 10 made in accordance with the preferred embodiment may be implanted below the skin of a patient. The device has a port 14 into which a hypodermic needle can be inserted through the skin to inject a quantity of a liquid agent, such as a medication or drug. The liquid agent is delivered from device 10 through a catheter port 20 into a catheter 22. Catheter 22 is positioned to deliver the agent to specific infusion sites in a brain (B). Device 10 may take the form of the like-numbered device shown in U.S. Pat. No. 4,692,147 (Duggan), assigned to Medtronic, Inc., Minneapolis, Minn., commercially available as the Synchromed® infusion pump, which is incorporated by reference.

The distal end of catheter 22 terminates in a cylindrical hollow tube 22A having a distal end 115 implanted into a portion of the basal ganglia of the brain by conventional stereotactic surgical techniques. Additional details about end 115 may be obtained from pending U.S. application Ser. No. 08/430,960, now abandoned, entitled "Intraparenchymal Infusion Catheter System," filed Apr. 28, 1995 in the name of Dennis Elsberry et al. and assigned to the same assignee as the present application. Tube 22A is surgically implanted through a hole in the skull 123 and catheter 22 is implanted subcuticularly between the skull and the scalp 125 as shown in FIG. 1. Catheter 22 is joined to implanted device 10 in the manner shown and may be secured to device 10 by, for example, ligating of catheter 22 onto catheter port 20. Device 10 is implanted in a human body in a subcutaneous pocket located in the chest below the clavicle. Alternatively, device 10 may be implanted in an abdomenal subcutaneous pocket.

In a second embodiment, distal end 115 of cylindrical hollow tube 22A may be implanted in a ventricle of the brain. Alternatively, the distal tip may be located in the subdural area beneath the dura under the skull 123 but outside the brain B, and within the arachnoidal space.

Catheter 22 may be divided into twin tubes 22A and 22B (not shown) that are implanted into the brain bilaterally. Alternatively, tube 22B (not shown) implanted on the other side of the brain may be supplied with drugs from a separate catheter and pump.

A sensor 130 is implanted into a portion of a patient's central nervous system. As shown in FIG. 1, sensor 130 comprises a sensing lead 26 having two sensing electrodes 28 and 30 located in the subthalamic region, substantia nigra or other brain region whose electrical activity indicates the degeneration of the neurons or the dysfunction of neurons communicating with the degenerating neurons. In particular, the sensor may indicate the activity of the degenerating neurons or related neurons which may be exhibiting hyperexcitation. Alternatively, electrodes 28 and 30 could be carried by lead 22A. Electrodes 28 and 30 are connected to an analog to digital converter 140 (FIG. 2) by conductors 134 and 135 which are located within catheter 22. The potentials sensed by electrodes 28 and 30 indicate the electrical excitatory activity in the subthalamic nucleus consequently projected to the substantia nigra and internal segment of the globus pallidus. Electrodes 28 and 30 transmit a signal related to the excitation of the portion of the brain exhibiting hyperexcitation. More specifically, electrodes 28 and 30 sense an attribute of the nervous system which indicates the hyperexcitation of the nerve cells projecting onto the degenerating affected nerve cells. Sensor 130 may take the form of a device capable of detecting nerve cell electrical activity that is related to the hyperexcitation. Such a sensor may be located deep in the brain. For such detecting function, sensor 130 may take the form of an electrode inserted into one of the nuclei of the basal ganglia, the thalamus, the internal capsule or the cortex of the brain. Signals that are received by the sensor may by amplified before transmission to circuitry contained within device 10.

Alternatively, sensor 130 may electronically transduce the concentration of a transmitter substance infused into the brain or released endogenously. A paper describing such a sensor is entitled "Multichannel Semiconductor-based Electrodes for In Vivo Electrochemical and Electrophysiological Studies in Rat CNS", by van Horne et al., 120 *Neuroscience Letters* 249–252 (Elsevier Scientific Publishers Ireland Ltd. 1990).

More particularly, the van Horne paper states:

The multichannel (5 recording sites per sensor) semiconductor-based probes were fabricated by the Center for Integrated Sensors and Circuits, at the University of Michigan, Ann Arbor [2]. The probes were fabricated using the high-yield approaches developed by Najafi at al. [15]. * * * The 5 individual recording sites were sputter-coated with 500 nm of carbon. The electrodes were then wire-bonded to a circuit board carrier for the acute recordings in anesthetized animals (see below) and were dip-coated with Nafion [7–9] to convert them into voltam-metric recording sensors. Four different designs were employed for the present investigations, which varied in recording site area The electrode recording sites on the silicon substrate were each positioned 200 $\mu$m from the center of the adjacent site in series, and the 5-channel electrodes spanned a recording area of 1 mm in all 4 electrode designs. The total surface areas of each type multichannel probe were 1000 (n=2), 2000 (n=2), 4000 (n=4), and 8000 $\mu m^2$ (n=5) per recording site. All 4 of the probe designs for high-speed electrochemical investigations while only the 1000, 2000, and 4000 $\mu m^2$ surface area electrodes were employed for both electrochemical and electrophysiological investigations (see below).

[2] BeMent, S. L., Wise, K. D., Anderson, D. J., Najafi, K. and Drake, K. L., Solid-state electrodes for multichannel multiplexed intracortical neuronal recording, IEEE Trans. Biomed. Eng., 2 (1986) 230–241, * * *
[7] Gerhardt, G. A., Oke, A. F., Nagy, G., Moghaddam, B. and Adam, R. N., Nafion-coated electrodes with high selectivity for CNS electrochemistry, Brain Res., 290 (1984) 390–395,
[8] Gerhardt, G. A., Rose. G. M. and Hoffer. B. J., Release of monoamines from striatum of rat and mouse evoked by local application of potassium: Evaluation of a new in vivo electrochemical technique, J. Neurochem., 46 (1986) 842–850.
[9] Gratton, A., Hoffer, B. J. and Gerhardt, G. A., In vivo electrochemical determination of monoamine release in the medial prefrontal cortex of the rat, Neuroscience, 29 (1989) 57–64. * * *
[15] Najafi, N. and Wise, K. D., A high-yield IC-compatible multichannel recording array, IEEE Trans. Electron Devices, 32 (1985) 1206–1211. * * *

Male Sprague-Dawley Rats (250–300 g) were anesthetized with urethane (1.25 g/kg), incubated, and placed in a stereotaxic frame for both in vivo electrochemical and electrophysiological studies. Electrochemical recordings were performed in the rat striatum and medial prefrontal cortex as determined by stereotaxic electrode placement [17]. All in vivo electrochemical measurements were performed using a high-speed chronoamperometric recording system (IVEC-5; Medical Systems Corp.) The multichannel probes were characterized for sensitivity to dopamine. norepinephrine and serotonin in vitro, and their selectivities to these compounds versus ascorbic acid were characterized. [van Horn paper at pp. 249–50]. * * *

[17] Paxinos, G. and Watson, C., The Rat Brain in Stereotaxic Coordinates Academic Press, New York, 1982. * * * [van Horne paper at p. 252 ].

This study provides the first documentation that Nafion-coated semiconductor-based multichannel recording electrodes can be used to quantitatively measure monoamines both in vitro and in vivo using high-speed chronoamperometric recording techniques, and that the same multichannel probes can be used for single-unit electrophysiological recordings. Moreover, electrophysiology experiments that require long recording times, such as those analyzing drug dose-effect relationships, can be investigated with these probes. * * * [van Horne paper at pp.251–51 ].

Figure 2A:
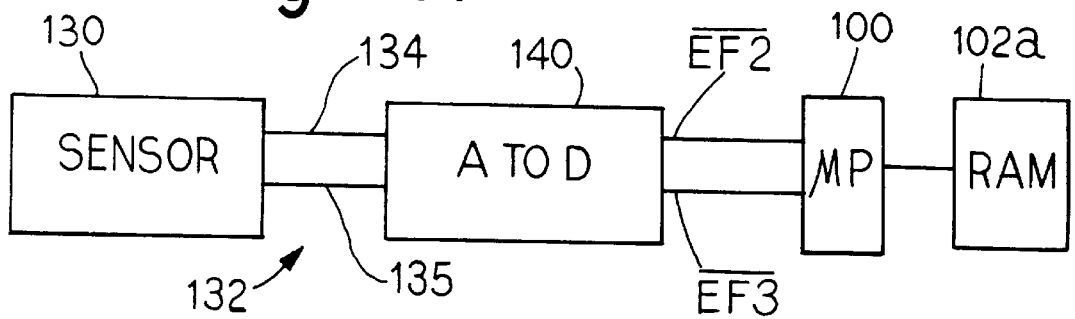
FIG. 2A is a schematic block diagram of a sensor and analog to digital converter circuit used in the preferred embodiment of the invention.

Referring to FIG. 2A, the output of sensor 130 is coupled by a cable 132 comprising conductors 134 and 135 to the input of analog to digital converter 140. The output of the analog to digital converter is connected to terminals EF2 BAR and EF3 BAR shown in FIG. 11A of U.S. Pat. No. 4,692,147 ("'147 Patent"). Before converter 140 is connected to the terminals, the demodulator currently shown in FIG. 11A of the '147 Patent would be disconnected.

The present invention may be implemented by providing several different dosages of nerve growth factors from 0 dosage to a 0.1 ml dosage with 0.005ml increments between choices. The time interval between dosages can be selected between one and twelve hours in seven choices. This is a scaled type of dosages compared to the typical dosage forms and interval described in connection with device 10 shown in the '147 Patent (column 5, beginning at line 63). The seven dosages and corresponding time increments may be loaded into RAM 102a in FIG. 2. The appropriate dosage and interval is selected by a computer algorithm that reads the output of converter 140 and makes the appropriate selection.

Figure 3:
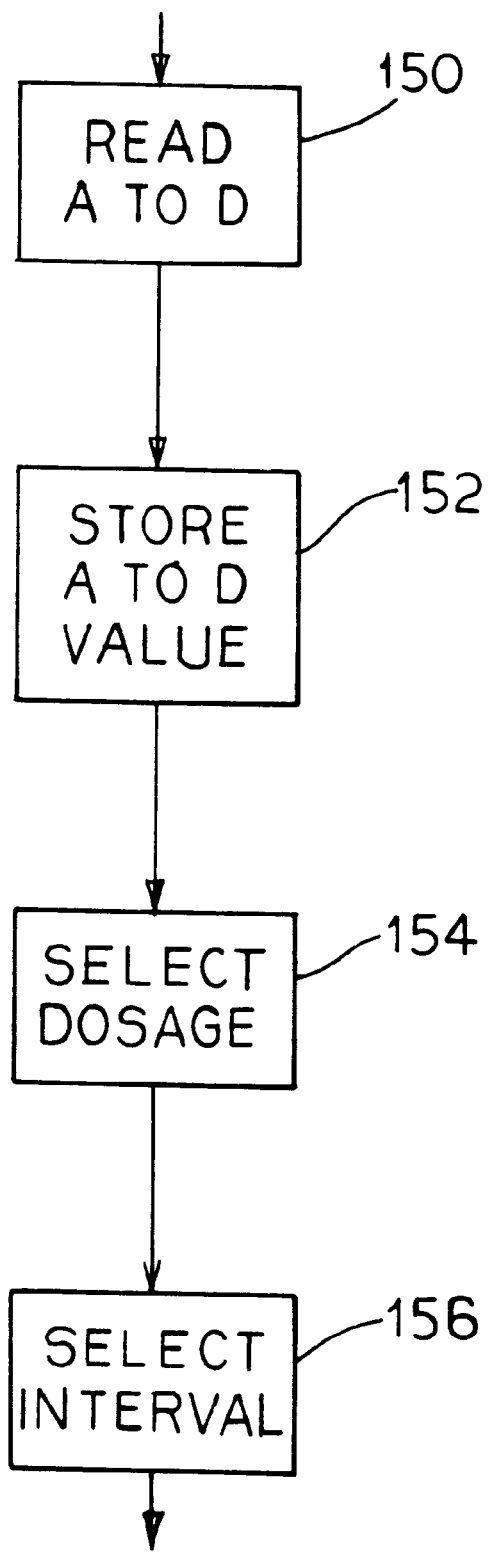
FIG. 3 is a flow chart illustrating a preferred form of a microprocessor program for utilizing the sensor to control the dosage of drug administered to the brain.

One exemplary computer algorithm is shown herein at FIG. 3, and is described as follows with particular reference to FIGS. 2A and 3 herein. Microprocessor 100 included within device 10 reads converter 140 in step 150, and stores one or more values in RAM 102a in step 152. One of seven dosages is selected in step 154, and an appropriate time interval is selected in step 156. The selected dosage and interval of a growth factor is then delivered through catheter 22 and tube 22A to the basal ganglia or other locations of the brain as described in the '147 Patent.

Figure 2B:
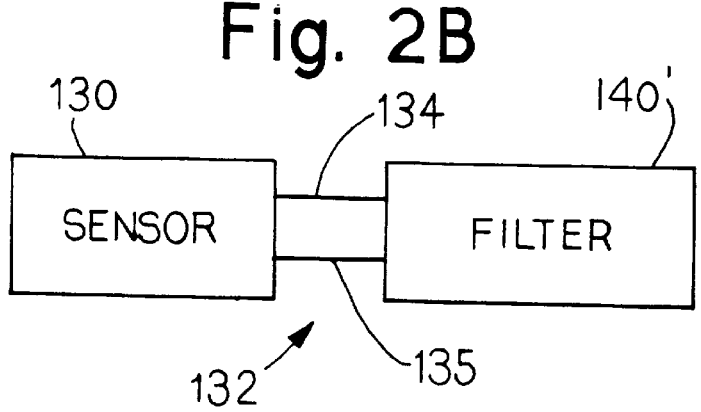
FIG. 2B is a schematic block diagram of a sensor and filter circuit in another preferred embodiment of the invention.

For some types of sensor, as shown in FIG. 2B a microprocessor and analog to digital converter will not be necessary. The output from sensor 130 can be filtered by an appropriate electronic filter 140 in order to provide a control signal for a pump of the type shown in the '147 Patent.

The type of growth factors administered by device 10 into the brain depend on the specific location at which distal end 115 of tube 22A is surgically implanted. The appropriate drugs for use in connection with the portion of the brain in which tube 22A terminates, together with the effect of the growth factor on that portion of the brain is provided in the following Table I:

TABLE I

| DAILY DOSING RANGE (micrograms) | EFFECT | PORTION OF BRAIN | DRUG |
|---|---|---|---|
| 0.5–2.0 | survival of cholinergic neurons | Basal forebrain and hippocampus | NGF |
| 0.5–2.0 | survival of cholinergic neurons | NBM Nucleus Basalis of Meynert | NGF |
| 1–5 | survival of cholinergic neurons | hippocampus | BDNF |
| 0.5–5 | survival of cholinergic neurons | hippocampus | NT-3 |
| 1–5 | survival of dopaminergic | striatum | CNTF |
| 1–5 | protection against excitotoxic neuronal damage | hippocampus | IGF-1 |
| 1–100 | neuritic outgrowth dopaminergic and neuronal survival | substantia nigra | GDNF |
| 1–100 | neuritic outgrowth dopaminergic and neuronal survival | striatum | GDNF |

In the foregoing Table I, the abbreviations used have the following meanings:
NGF Nerve growth factor
BDNF Brain-derived Neurotrophic Factor
NT-3 Neurotrophin-3
CNTF Ciliary Neurotrophic Factor
GDNF Glial-derived Neurotrophic Factor Stereotaxic coordinates for the portions of the brain described in Table I are identified in the following Table II:

TABLE II

| BRAIN REGION | MEDIAL-LATERAL DIMENSION | DORSAL-VENTRAL DIMENSION | ANTERIOR-POSTERIOR DIMENSION |
|---|---|---|---|
| Gpe | 1.6 to 2.7 | 1.0 to –1.0 | 2.0 to –1.0 |
| Gpi | 0.5 to 2.0 | 0.5 to –0.7 | 0.7 to 2.0 |
| SNr | 0.5 to 1.5 | –0.6 to –1.5 | 0.7 to –0.7 |
| STN | 0.5 to 2.0 | 0.0 to –1.0 | 0.6 to –1.0 |
| NBM | 1.5 to 2.5 | 0.0 to –1.2 | 0.5 to 1.6 |
| Striatum: caudate | 0.5 to 2.0 | 1.5 to 3.0 | 1.5 to 3.0 |
| putamen | 1.2 to 3.3 | 1.5 to –1.0 | 2.5 to –1.2 |

In the foregoing table: the medial-lateral dimensions are relative to midline of the brain; the anterior-posterior dimensions are relative to the midpoint between the anterior commissure and posterior commissure with negative indicating the posterior direction; the dorsal-ventral dimensions are relative to a line connecting the midpoints of the anterior and posterior commissures with negative being ventral to said line; all dimensions are in centimeters; and Gpe means external segment of globus pallidus; Gpi means internal segment of globus pallidus; Snr means substantia nigra pars reticulata; STN means subthalamic nucleus; NBM means nucleus basalis of meynert; and caudate means caudate nucleus.

Preferred ranges of dosages and specific drugs for the brain infusion sites identified in Tables I are provided in the following Table III:

TABLE III

| NEURONAL TYPE | SPECIFIC DRUG | DAILY DOSING RANGE (micrograms) |
|---|---|---|
| cholinergic | NGF | 0.5–2.0 |
| cholinergic | BDNF | 1.0–5.0 |
| cholinergic | NT-3 | 0.5–5.0 |
| dopaminergic | CNTF | 1.0–5.0 |
| glutaminergic | IGF-1 | 1.0–5.0 |
| dopaminergic | GDNF | 1.0–100 |

Microprocessor 100 within device 10 can be programmed so that a controlled amount of growth factor can be delivered to the specific brain sites described in Tables I and III. Alternatively, sensor 130 can be used with a closed loop feedback system in order to automatically determine the level of drug delivery necessary to alleviate the hyperexcitation as described in connection with FIG. 3.

By using the foregoing techniques, motor disorders can be controlled with a degree of accuracy previously unattainable.

Those skilled in that art will recognize that the preferred embodiments may be altered or amended without departing from the true spirit and scope of the invention, as defined in the accompanying claims.

We claim:

1. A method of treating a neurodegenerative disorder by means of an implantable pump and a catheter having a discharge portion and having a proximal end coupled to said pump, said method comprising the steps of:

implanting said pump outside a brain subject to nerve degeneration;

surgically implanting said catheter so that said discharge portion lies adjacent a predetermined infusion site in said brain;

operating said pump to discharge a predetermined dosage of one or more nerve growth factors through said discharge portion of said catheter into said infusion site; and periodically refreshing the supply of said one or more nerve growth factors to said pump outside said brain, whereby further neurodegeneration is prevented and said neurodegenerative disorder is therapeutically treated.

2. A method, as claimed in claim 1, wherein said step of implanting said catheter is performed as soon as practical after said neurodegenerative disorder is diagnosed.

3. A method, as claimed in claim 1, wherein said neurodegenerative disorder is Parkinson's; and wherein said predetermined infusion site is selected from the group consisting of the substantia nigra pars reticulata (SNr) and the neostriatum.

4. A method, as claimed in claim 1, wherein said neurodegenerative disorder is amyotrophic lateral sclerosis; and wherein said predetermined infusion site is selected from the group consisting of the intraventricular space and the subdural space.

5. A method, as claimed in claim 1, wherein said neurodegenerative disorder is Alzheimer's disease; and wherein said predetermined infusion site is selected from the group consisting of the intraventricular space, the subdural space, the hippocampus and the nucleus basalis of meynert.

6. A method, as claimed in claim 1, further comprising the step of:

implanting a sensor into a portion of a central nervous system of a patient.

7. A method, as claimed in claim 6, further comprising the step of:

sensing an attribute of a nervous system which indicates degeneration of neurons that may exhibit hyperexcitation.

8. A method, as claimed in claim 7, further comprising the step of:

sensing an attribute of a nervous system which indicates the activity of neurons related to degenerating neurons that may exhibit hyperexcitation.

9. A method of claim 6, wherein the step of implanting includes the step of implanting the sensor in a brain.

10. A method as claimed in claim 6, further comprising the steps of:

generating a sensor signal indicating a manifestation of said neurodegenerative disorder; and regulating said pump to alter said predetermined dosage based on the extent of said neurodegenerative disorder.

11. A method as claimed in claim 10, wherein the step of regulating includes the step of altering a time interval of said predetermined dosage.

12. A method as claimed in claim 1, wherein said one or more nerve growth factors is selected from the group consisting of NGF, BDNF, NT-3, CNTF, IGF-1 and GDNF.

13. A system for treating a neurodegenerative disorder resulting in degenerating neurons forming part of a nervous system comprising in combination:

a pump implanted outside a brain subject to nerve degeneration;

a catheter having a proximal end coupled to said pump and a discharge portion for infusing into a predetermined infusion site in said brain a therapeutic dosage of one or more nerve growth factors;

a sensor for generating a signal related to an attribute of said nervous system which indicates the degeneration of said degenerating neurons or the degeneration of neurons related to said degenerating neurons; and control means responsive to said sensor signal for regulating said therapeutic dosage.

14. A system, as claimed in claim 13, wherein said sensor comprises means for indicating the hyperexcitation of said degenerating neurons or neurons related to said degenerating neurons.

15. A system, as claimed in claim 13, wherein said sensor comprises means for detecting the extent of the hyperexcitation of the glutamatergic neurons of said brain.

16. A system, as claimed in claim 15, wherein said control means comprises means for increasing said therapeutic dosage in response to an increase in said hyperexcitation and for decreasing said therapeutic dosage in response to a decrease in said hyperexcitation.

17. A system, as claimed in claim 13, wherein said sensor comprises means for detecting changes in potentials of or electromagnetic waves generated by said nervous system.

18. A system, as claimed in claim 13, wherein said sensor comprises means for detecting neurotransmitters or their metabolites.

19. A system, as claimed in claim 13, wherein said control means comprises a microprocessor.

20. A system, as claimed in claim 13, wherein said control means comprises an electrical filter.

21. A system as claimed in claim 13, wherein said sensor includes at least one electrode suited to sense electrical activity.

22. A system as claimed in claim 6, wherein said sensor is suited to transduce concentration of a transmitter substance.

23. A system as claimed in claim 13, further comprising an analog to digital converter coupling the sensor to the control means.

* * * * *